United States Patent
Weigold et al.

[19]

[11] Patent Number: 5,808,461
[45] Date of Patent: Sep. 15, 1998

[54] CIRCUIT ARRANGEMENT FOR AIR QUALITY MEASUREMENT WITH LOGARITHMIC SIGNAL EVALUATION

[75] Inventors: Thomas Weigold, Sinzheim; Heiner Holland, Freiburg, both of Germany

[73] Assignee: Robert Bosch GmbH, Stuttgart, Germany

[21] Appl. No.: 688,158

[22] Filed: Jul. 29, 1996

[30] Foreign Application Priority Data

Jul. 27, 1995 [DE] Germany .......................... 195 27 426.1

[51] Int. Cl.[6] ..................................................... G01N 27/12
[52] U.S. Cl. ........................ 324/71.1; 324/713; 324/720; 73/31.01; 73/31.05
[58] Field of Search .................................. 324/71.1, 71.4, 324/71.5, 464, 691, 693, 705, 713, 720; 340/633; 454/75; 73/31.01, 31.02, 31.03, 31.05; 96/18, 22, 23, 24, 25; 250/338.5; 422/94, 98

[56] References Cited

U.S. PATENT DOCUMENTS

| | | | |
|---|---|---|---|
| 3,761,724 | 9/1973 | Dennis . | |
| 3,906,473 | 9/1975 | Le Vine | 324/71.4 |
| 4,012,692 | 3/1977 | Eicker | 324/71.1 |
| 4,542,640 | 9/1985 | Clifford | 73/31.05 |
| 4,818,977 | 4/1989 | Alexander | 340/633 |
| 5,061,447 | 10/1991 | Ono | 324/720 |

FOREIGN PATENT DOCUMENTS 3825036  1/1990  Germany .

OTHER PUBLICATIONS

Soviet Inventions Illustrated, Chemical Section, Week 84/22; Derwent Publications Ltd., London; & SU–A–1036 767 (Electro Thermic APP).

Primary Examiner—Diep N. Do
Attorney, Agent, or Firm—Spencer & Frank

[57] ABSTRACT

A circuit arrangement for air quality measuring having at least one sensor element which has resistors the resistance of which changes depending on the air composition. The circuit arrangement has an evaluation circuit for the sensor signals and includes a logarithmic circuit.

8 Claims, 4 Drawing Sheets

CIRCUIT ARRANGEMENT FOR AIR QUALITY MEASUREMENT WITH LOGARITHMIC SIGNAL EVALUATION

CROSS-REFERENCE TO RELATED APPLICATION

This application claims the priority of patent application Ser. No. 1 95 27 426.1-52 filed in Germany on Jul. 27, 1995, the subject matter of which is incorporated herein by reference.

BACKGROUND OF THE INVENTION

The present invention relates to a circuit arrangement for air quality measurement, which circuit arrangement has at least one sensor element having resistors the resistance value of which changes depending on the air composition as well as a circuit for evaluating signals put out by the sensor element.

There exist circuit arrangements for air quality measurement having at least one sensor element with one resistor, which changes its amount of resistance, depending on a certain pollutant concentration in an air composition. In particular, such circuit arrangements are known to be used for measuring the proportion of carbon monoxide or nitrogen oxide in an air composition. Because of a changing air composition, the sensor element readies an output signal, which can be used, for example with the aid of an evaluation circuit, to trigger a certain reaction to the change in the air composition. It is known in this connection that the ventilation system operation in motor vehicles is switched from fresh air to recirculation of air because of a change, and especially an increase in the concentration of carbon monoxide or nitrogen oxide. This is to prevent a pollution-burdened outside air from reaching the inside area of the motor vehicle.

An arrangement with such a circuit is shown, for example, in DE-OS 38 25 036. One disadvantage of such circuit arrangements is that the basic resistance of the sensor elements used can be subject to strong fluctuation in batches and/or over the life expectancy of the sensor elements. These fluctuations can vary, for example, from a few k$\Omega$ to more than 100 k$\Omega$, so that misinterpretations of the actual concentration of the air composition can occur and thus also lead to a faulty output signal. One additional disadvantage is that if the sensor elements are used as specified, their sensor surfaces become dirty and thus low-ohmic. As a result of this, the measuring current flowing through the sensor element increases, which can lead to an impairing of the evaluation circuit for the sensor element output signal.

SUMMARY OF THE INVENTION

In contrast, the circuit arrangement according to the invention, which incorporates an evaluation circuit having a logarithmic circuit, has the advantage of offering a constant sensitivity, independent of the basic resistance of the sensor element. Due to the fact that the evaluation circuit has a logarithmic circuit, it is also possible to make a logarithmic evaluation of the characteristic curve for the logarithmic resistance/concentration of the sensor element and obtain a logarithmic characteristic curve of the output signal that is adapted to the behavior of the sensor element.

According to a preferred embodiment of the circuit arrangement according to the present invention, the measuring current can be adjusted with the sensor elements and, preferably, can be limited to a maximum value. This has the advantage that for a circuit arrangement with two sensor elements, where each element detects a different concentration of the air composition, the measuring currents can be adjusted with the aid of the sensor elements. Furthermore, it is possible to make an advantageous adjustment of the measuring currents in cases where the two sensor elements of the circuit arrangement have basic resistances that differ considerably. The adjustment or adaptation of the measuring currents can easily be made with a voltage divider. In addition, in another preferred embodiment of the circuit arrangement, the measuring current is limited to a maximum value, the arrangement preferably incorporating a current-limiting resistance. Another advantageous embodiment of the circuit arrangement is so constructed that it can function optionally either with one or both sensor elements. In that case, it is preferable if the sensor element that is not needed is replaced by a fixed resistor. It is also extremely advantageous to make possible a relative weighting of the sensor signals supplied by the two sensor elements provided for in the circuit arrangement. As a result of this, the sensitivities of the sensor elements measuring the nitrogen oxide concentration or the carbon monoxide concentration can be coordinated, so that the total output signal readied by the circuit arrangement reacts more strongly to a change in the nitrogen oxide concentration or a change in the carbon monoxide concentration.

In a further advantageous embodiment of the circuit arrangement, a transverse strain sensitivity compensation can be provided for the sensor element detecting the nitrogen oxide concentration. The relatively strong transverse strain sensitivity to a carbon monoxide concentration here can be compensated for quite advantageously with the evaluation circuit.

BRIEF DESCRIPTION OF THE DRAWINGS

These and other features and advantages of the invention will be further understood from the following detailed description of the preferred embodiments with reference to the accompanying drawings in which.

DETAILED DESCRIPTION OF THE PREFERRED EMBODIMENTS

Figure 1:
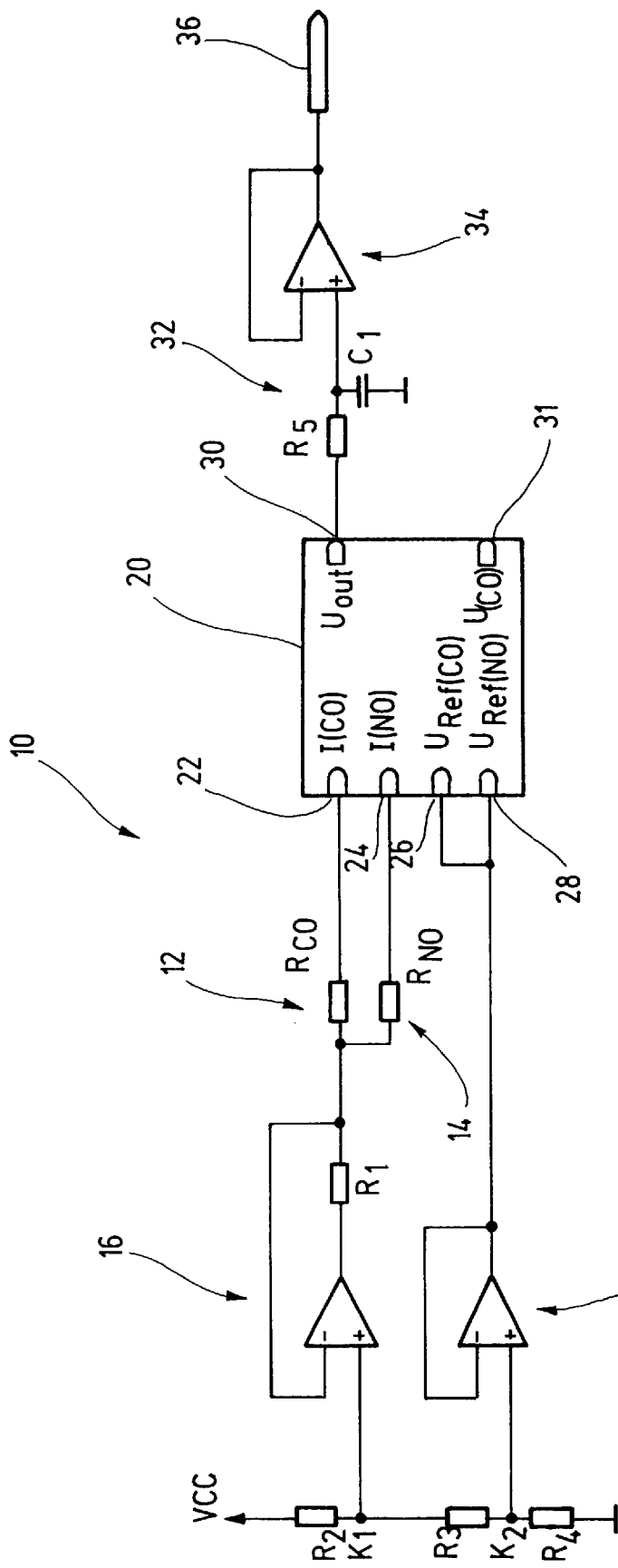
FIG. 1 illustrates a first embodiment of a circuit arrangement according to the present invention.

FIG. 1 shows a circuit arrangement 10 which is used to record an air composition, in particular the existing concentration of carbon monoxide and/or nitrogen oxide. This circuit arrangement 10 has a first sensor element 12 for detecting a carbon monoxide concentration. The sensor element 12 is represented by a resistor $R_{CO}$. A second sensor element 14 is provided which serves to detect a nitrogen oxide concentration. The sensor element 14 is represented by a resistor $R_{NO}$. The resistance values for resistor $R_{CO}$ or $R_{NO}$ depends on the concentrations of either carbon monoxide or nitrogen oxide. The resistors $R_{CO}$ and $R_{NO}$ are connected via a resistor R1 with the output of a first operational amplifier 16. Operational amplifier 16 is connected as a non-inverting amplifier. The non-inverting input of operational amplifier 16 is connected to a nodal point K1, which is located between two series-connected resistors R2 and R3. Another resistor R4 is also connected in series with resistors R2 and R3. A nodal point K2, which is located between resistors R3 and R4, is connected to the non-inverting input of a second operational amplifier 18. The second operational amplifier 18 is also connected as a non-inverting amplifier.

The circuit arrangement 10 also has an evaluation circuit 20. A first input 22 of evaluation circuit 20 is connected to resistor $R_{CO}$, a second input 24 is connected to resistor $R_{NO}$. Furthermore, a third input 26 as well as a fourth input 28 of the evaluation circuit 20 are connected to the output of operational amplifier 18. A first output 30 of the evaluation circuit 20 is connected to a low-pass filter 32 which comprises a resistor R5 and a capacity C1. The low-pass filter 32 is connected to the non-inverting input of a third operational amplifier 34, which is also connected as a non-inverting amplifier. The output of operational amplifier 34 is connected to an output connection 36 of the circuit arrangement 10. The evaluation circuit 20 furthermore has a second output 31.

Figure 2:
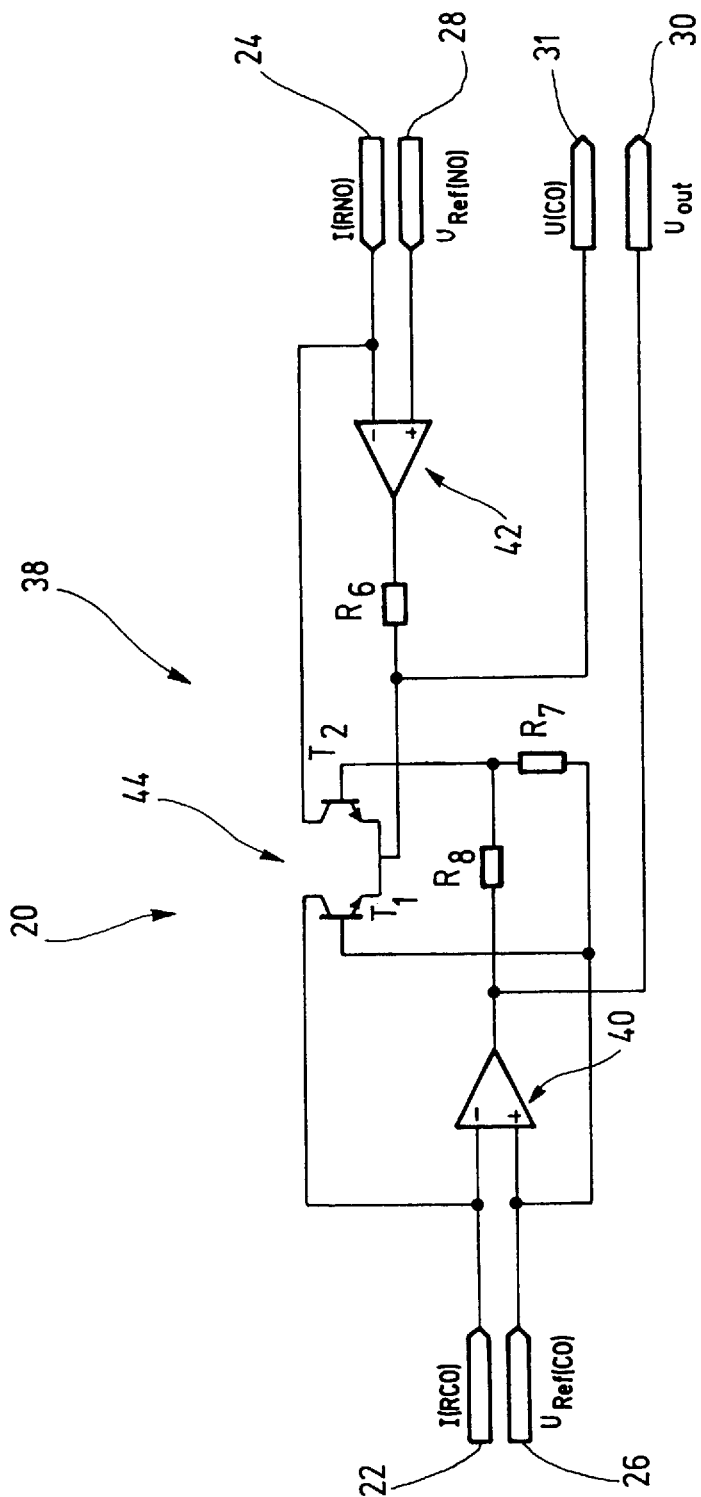
FIG. 2 illustrates a circuit arrangement for the evaluation circuit.

The evaluation circuit 20 is set up as a logarithmic circuit 38, as shown in more detail in FIG. 2. The logarithmic circuit 38 has the circuit design shown in FIG. 2, wherein any other optional circuit design can be used, which can represent a logarithmic function. Inputs 22 and 26 are linked to an operational amplifier 40 and inputs 24 and 28 are linked to an operational amplifier 42. Inputs 22 and 24, which are connected to resistors $R_{CO}$ or $R_{NO}$ (FIG. 1), are here connected respectively to the inverting inputs of operational amplifiers 40 or 42, while the inputs 26 and 28 are connected to the respective non-inverting inputs of operational amplifiers 40 and 42. Furthermore, there is a differential amplifier circuit 44 of transistors T1 and T2, with the transistors T1 and T2 being npn-transistors. The collector for transistor T1 is connected to input 22, the base of transistor T1 is connected to input 26 and the emitter of transistor T1 is connected via a resistor R6 to the output of operational amplifier 42 and to the output 31 of evaluation circuit 20. The collector for transistor T2 is connected to input 24, the base of transistor T2 is connected via a resistor R7 to the input 26 and the emitter of transistor T2 is also connected via the resistor R6 to the output of operational amplifier 42 and the output 31. The output of operational amplifier 40 is connected to the output 30 of evaluation circuit 20 and via a resistor R8 to the base of transistor T2.

The circuit arrangement 10 shown in FIGS. 1 and 2 functions as follows:

The resistors R2, R3 and R4, which are connected in series, form a voltage divider for a supply voltage positioned between the outside connections for the series connection. A certain resistance value arises for resistor $R_{CO}$ or $R_{NO}$, depending on the actually existing concentration of carbon monoxide or nitrogen oxide. As a result of this, a measuring current $I_{CO}$ adjusts via resistor $R_{CO}$, which is present at input 22 of the evaluation circuit 20. Another measuring current $I_{NO}$ flows via resistor $R_{NO}$, which is applied to input 24 of the evaluation circuit 20. The measuring current for sensor element 12 or sensor element 14 is the result of the quotient of the respective sensor voltage and the concentration-dependent sensor resistor $R_{CO}$ or $R_{NO}$. This results in sensor voltage $U_{S(CO)}$ at sensor element 12 as well as sensor voltage $U_{S(NO)}$ at sensor element 14. The sensor voltage $U_{S(CO)}$ here is the result of the difference between the output voltage for operational amplifier 16 and the reference voltage $U_{Ref(CO)}$ present at input 26 for sensor element 12. The sensor voltage $U_{S(NO)}$ for sensor element 14 results from the difference of the output voltage for operational amplifier 16 and the reference voltage $U_{R(NO)}$ for sensor element 14, which is present at input 28. The sensor voltages $U_{S(CO)}$ or $U_{S(NO)}$ that occur at sensor elements 12 or 14 are the same because reference voltages $U_{R(CO)}$ and $U_{R(NO)}$ are equal. As a result of this, the measuring currents $I_{CO}$ or $I_{NO}$ occurring at inputs 22 or 24 change along with the change in the carbon monoxide concentration or the nitrogen oxide concentration.

The measuring current volume is adjustable via the voltage divider with resistors R2, R3, R4. In addition, very widely differing basic resistors $R_{CO}$ or $R_{NO}$ for sensor elements 12 or 14 can be adapted by selecting the resistors for voltage divider R2, R3, R4.

The resistor R1, which is connected in series between the output of operational amplifier 16 and the sensor elements 12 or 14, functions as a current limiter. This limiting is necessary, among other things, if the resistors $R_{CO}$ or $R_{NO}$ of sensor elements 12 or 14 become low-ohmic, for example, as a result of surface impurities. This would lead to an increase in the measuring currents $I_{CO}$ or $I_{NO}$. The output voltage for operational amplifier 16 cannot exceed a certain voltage value $U_{max}$, depending on the operational amplifier used. If the sum of sensor currents $I_{CO}$ and $I_{NO}$ exceeds a certain value, the output voltage for the operational amplifier 16 cannot rise any longer. As a result of this, the sensor voltage $U_{S(CO)}$ or $U_{S(NO)}$ drops and the sensor current is limited to maximum value $I_{max}$, which results from the difference of voltage $U_{max}$ and reference voltage $U_{R(CO)}$, divided by resistor R1.

The evaluation circuit 20, which is formed by logarithmic circuit 38, supplies an output signal $U_{out}$ to its output 30. In this case, measuring currents $I_{CO}$ and $I_{NO}$ or reference voltages $U_{R(CO)}$ and $U_{R(NO)}$, which are present at inputs 22 to 28, are processed by the logarithmic circuit 38. The output voltage signal here is obtained based on the following formula:

$$U_{out} = U_{Ref(CO)} - K_R \cdot U_T \cdot \ln \frac{R_{NO}}{R_{CO}}$$

$$\text{where: } K_R = \frac{R_7 + R_8}{R_7}$$

$$U_T \approx 26 \text{ mV (at } 20° \text{ C.)}$$

In accordance with logarithmic circuit 38, the output signal $U_{out}$ has a logarithmic characteristic curve that is adapted to the logarithmic behavior of the resistance values for resistors $R_{CO}$ or $R_{NO}$. Thus, a constant sensitivity for evaluation circuit 20 results over far ranges of the basic resistance of resistors $R_{CO}$ or $R_{NO}$.

The output signal $U_{out}$ is conducted via low-pass filter 32 and the operational amplifier 34. Voltage signal $U_{out}$ is filtered via the low pass filter 32 and is subsequently amplified in the operational amplifier 34, so that an output signal for circuit arrangement 10 is present at output connection 36, which can be used, for example, to activate a circuit arrangement for switching from fresh air to recirculated air in motor vehicles. Of course, this is simply one exemplary use because the output signal present at the output connection 36 can also be used for other purposes and for other embodiments.

The voltage sources here displayed as operational amplifiers 16, 18 or 34, can also be realized through other suitable components.

For certain applications, where only one sensor element 12 or 14 is to be used, one of the resistors $R_{CO}$ or $R_{NO}$, which has a variable resistance value, can be replaced by a fixed resistor.

Figure 3:
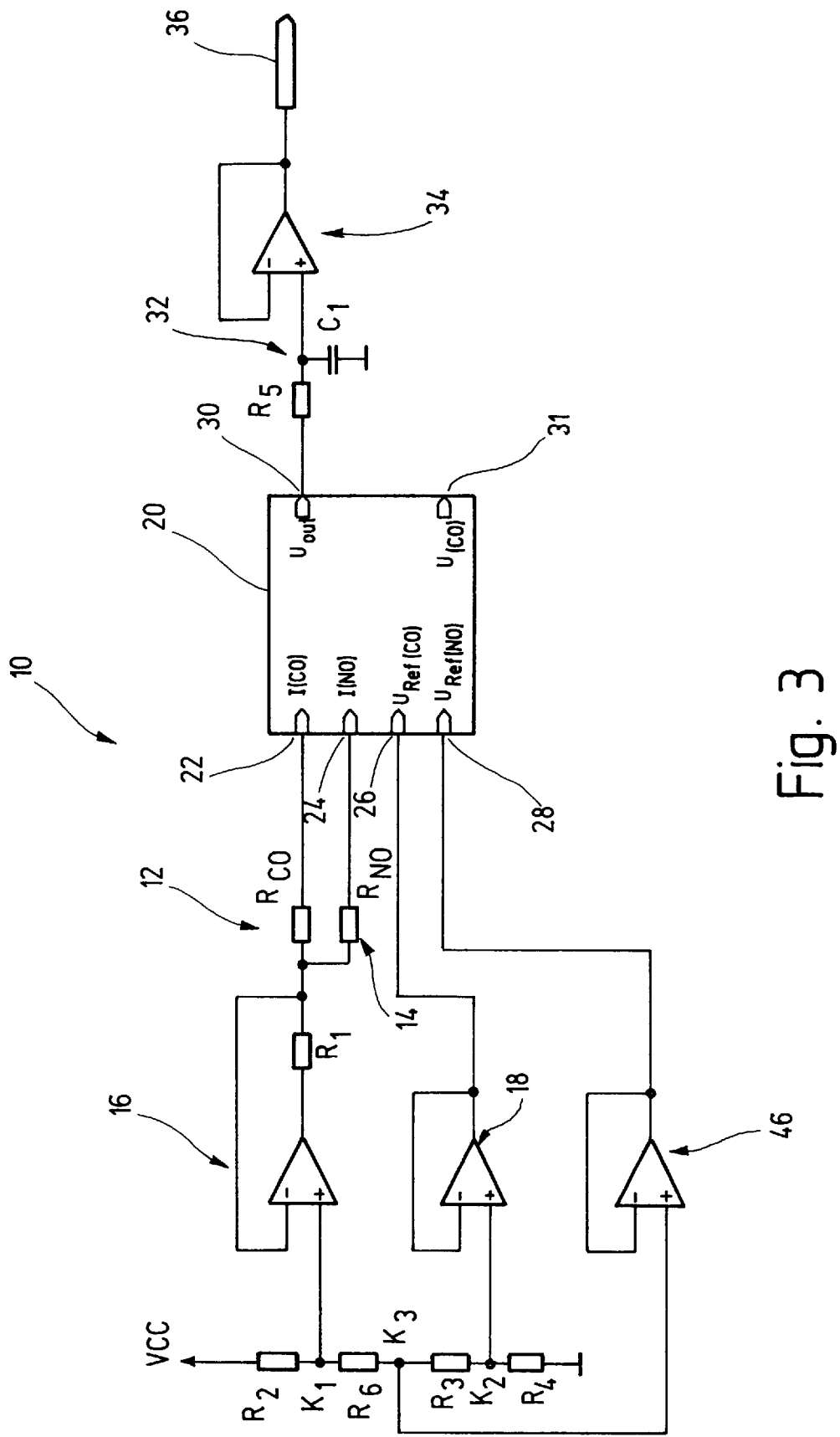
FIG. 3 illustrates a second embodiment of a circuited arrangement according to the present invention.

FIG. 3 shows another variation of an embodiment of the circuit arrangement 10, wherein the same components as in FIGS. 1 and 2 have the same reference numerals and are not explained again. Another resistor R6 is connected in series with resistors R2, R3 and R4. A nodal point K3 between resistors R3 and R6 is connected to a non-inverting input of another operational amplifier 46. The operational amplifier 46 is connected as a non-inverting amplifier, the output of which is connected to the input 28 of evaluation circuit 20. In contrast to the circuit arrangement in FIG. 1, the output for operational amplifier 18 is connected only to input 26 of evaluation circuit 20.

As result of the additional connection of operational amplifier 46, it is possible to adjust the reference voltages $U_{Ref(CO)}$ or $U_{Ref(NO)}$ for sensor elements 12 or 14 differently via the voltage divider for resistors R2, R6, R3 and R4. This permits a relative weighting of the sensor signals supplied by sensor elements 12 or 14, meaning the measuring currents $I_{CO}$ or $I_{NO}$. Varied reference voltages $U_{Ref(CO)}$ or $U_{Ref(NO)}$ result in different sensor voltages $U_{S(CO)}$ or $U_{S(NO)}$ at resistors $R_{CO}$ or $R_{NO}$ and thus also varied sensitivities of the sensor elements 12 or 14.

According to the circuit arrangement 10 shown in FIG. 3, the sensitivity of sensor element 12 is higher than the sensitivity of sensor element 14. By exchanging the reference voltages $U_{Ref(CO)}$ or $U_{Ref(NO)}$, applied to inputs 26 or 28 of evaluation circuit 20, the exact opposite sensitivity can be fixed for sensor elements 12 or 14.

At output 30 of circuit arrangement 20, which again contains the logarithmic circuit 38 shown in FIG. 2, an output voltage signal $U_{out}$ is applied according to the following equation:

$$U_{out} = U_{Ref(CO)} - K_R \cdot U_T \cdot \ln \frac{R_{NO} \cdot U_{S(CO)}}{R_{CO} \cdot U_{S(NO)}}$$

Figure 4:
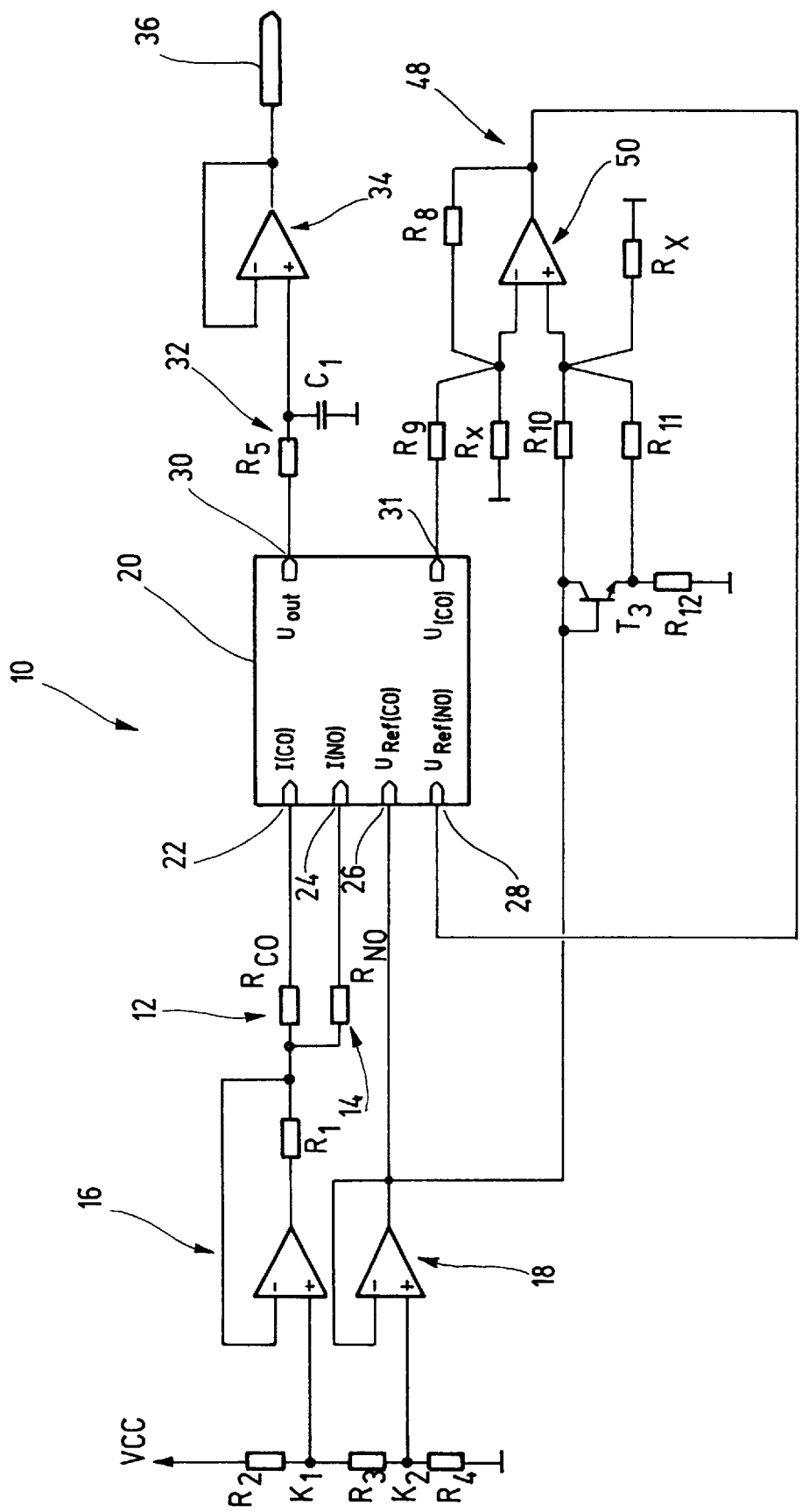
FIG. 4 illustrates a third embodiment for a circuit arrangement according to the present invention.

Another advantageous variation of the embodiment is explained with the aid of the circuit arrangement 10 shown in FIG. 4. As in the previously described figure, the same components carry the same reference numbers.

The output 31 of the evaluation circuit 20 here is connected via a compensation circuit 48 with the input 28 of evaluation circuit 20. The compensation circuit 48 includes an operational amplifier 50, for which the inverting input is connected via a resistor R9 with the output 31 of evaluation circuit 20. The non-inverting input of operational amplifier 50 is connected via a resistor R10 with the output of operational amplifier 18. The output of the operational amplifier 18 continues to be connected with the base and the collector of a transistor T3. The emitter for transistor T3 is connected via a resistor R11 with the non-inverting input of operational amplifier 50. Furthermore, resistors R12 and another resistor, simply called Rx, are provided here, which serve to trigger operational amplifier 50.

With the compensation circuit 48 shown in FIG. 4, an evaluation can be made of the voltage $U_{CO}$, which is present at output 31 of evaluation circuit 20 and which corresponds to the carbon monoxide concentration measured via sensor element 12. Transistor T3 here represents a temperature compensation for transistor T1, which is a part of logarithmic circuit 38. Thus, a voltage signal is present at the operational amplifier 50, which depends on the carbon monoxide concentration and which serves as reference voltage $U_{R(NO)}$ for sensor element 14, meaning the nitrogen oxide sensor element. Thus, a relative weighting, depending on the carbon monoxide concentration, is possible of both the sensor signals supplied by sensor elements 12 or 14.

For the circuit arrangement 10 shown in FIG. 4, the evaluation circuit 20 supplies an output voltage signal $U_{out}$ at its output 30, based on the following equation:

$$U_{out} = U_{Ref(CO)} - K_R \cdot U_T \cdot \ln \frac{R_{NO}}{R_{CO}} +$$

$$K_R \cdot U_T \cdot \ln \left( 1 + \frac{U_T{}^v}{U_{S(CO)}} \cdot \ln \frac{U_{S(CO)}}{R_{CO} \cdot I_{R12}} \right)$$

with:

$$v = \frac{R_X}{R_9}$$

$$R_9 = R_{11} \text{ und } R_X = R_{10}$$

All in all, the circuit arrangements 10 shown in FIGS. 1 to 4 make it possible to record a change in the resistance of resistors $R_{CO}$ or $R_{NO}$, which depends on the carbon monoxide concentration or the nitrogen oxide concentration, and to link the sensor signals supplied by sensor elements 12 or 14. In this case, the evaluation circuit 20 has a constant sensitivity, independent of the basic resistances for sensor elements 12 or 14. Furthermore, the measuring current flowing through sensor elements 12 or 14 is adjustable and can be limited to a maximum value. In addition, the sensor signals supplied by sensor elements 12 or 14 can be weighted relative to each other, wherein it is also possible to compensate for a relatively strong transverse sensitivity of the nitrogen oxide sensor element 14 to a carbon monoxide concentration. Through simple replacement of one of the concentration-dependent resistors $R_{CO}$ or $R_{NO}$ with a fixed resistor, the complete circuit arrangement 10 can be operated selectively with just one sensor element 12 or 14. Thus, circuit arrangement 10 can be used under all conditions, its simple design notwithstanding and can readily be adapted to existing conditions.

It will be understood that the above description of the present invention is susceptible to various modifications, changes and adaptations, and the same are intended to be comprehended within the meaning and range of equivalents of the appended claims.

What is claimed is:

1. Circuit arrangement for air quality measurement comprising: first and second sensor elements for providing respective first and second measuring signals which change as a function of a change of respective components of the air composition, with the first sensor element including a first resistor ($R_{CO}$) for detecting a first gas component of the air and whose resistance value change as a function of the concentration change of the first gas component, and with the second sensor element including a second resistor ($R_{NO}$) for detecting a second gas component of the air and whose resistance value changes as a function of the concentration change of the second gas component; and an evaluation circuit for evaluating the measuring signals to provide an output signal indicative of the concentration of the first and second components, said evaluation circuit including a single logarithmic circuit means, having first and second active inputs connected respectively to the first and second resistors for receiving the respective measuring signals, and for producing a change in said output signal representative of a change of the resistance value of either of the first and second resistors.

2. Circuit arrangement according to claim 1, wherein said logarithmic circuit means is connected with reference voltage sources for said resistors.

3. Circuit arrangement according to claim 2, wherein said first and second resistors and said reference voltage sources are connected via a voltage divider with a supply voltage.

4. Circuit arrangement according to claim 3, further comprising a current limiter connected between said voltage divider and said first resistor.

5. Circuit arrangement according to claim 2, wherein said reference voltage sources provide equal reference voltages.

6. Circuit arrangement according to claim 2, wherein the reference voltages are adjustable for varied amounts.

7. A circuit according to claim 2, wherein the resistance of said first resistor changes depending on the carbon monoxide concentration of the air; said evaluation circuit has a further output at which a signal which corresponds to the carbon monoxide concentration of the air is provided; and, a compensating circuit is connected to said further output and delivers the reference voltage for the first resistor.

8. A circuit according to claim 1, wherein the resistance of said first resistor changes depending on the concentration of carbon monoxide in the air, and wherein the resistance of said second resistor changes depending on the concentration of nitrogen oxide in the air.

* * * * *